United States Patent [19]

Schulte

[11] 4,190,040
[45] Feb. 26, 1980

[54] RESEALABLE PUNCTURE HOUSING FOR SURGICAL IMPLANTATION

[75] Inventor: Rudolf R. Schulte, Santa Barbara, Calif.

[73] Assignee: American Hospital Supply Corporation, Evanston, Ill.

[21] Appl. No.: 921,559

[22] Filed: Jul. 3, 1978

[51] Int. Cl.² .................... A61B 19/00; A61F 1/00
[52] U.S. Cl. ........................................... 128/1 R; 3/1
[58] Field of Search ............... 3/1, 1.2, 36; 128/1 R, 128/346, DIG. 25, 350 V

[56] References Cited

U.S. PATENT DOCUMENTS

| 3,831,583 | 8/1974 | Edmunds, Jr. et al. ............. 128/1 R |
| 3,919,724 | 11/1975 | Sanders et al. ........................... 3/1 X |
| 3,934,274 | 1/1976 | Hartley, Jr. ............................... 3/36 |

OTHER PUBLICATIONS

Heyer–Schulte Introductory Data Sheet, Radovan Subcutaneous Tissue Expander, Apr. 1977.

Primary Examiner—Ronald L. Frinks
Attorney, Agent, or Firm—Larry N. Barger

[57] ABSTRACT

A puncturable resealable housing for surgical implantation beneath the skin and which is adapted to receive repeated hypodermic punctures through the skin and into the housing. The housing has an improved dimensional and shape configuration of a sealant layer to receive hypodermic punctures from widely angled positions.

11 Claims, 3 Drawing Figures

RESEALABLE PUNCTURE HOUSING FOR SURGICAL IMPLANTATION

BACKGROUND

A related patent application Ser. No. 723,338 now abandoned, and refiled as Ser. No. 926,484 on a Skin Flap Development Device, invented by Chadomir Radovan and myself, describes a surgically implantable puncture housing. This housing is joined to a highly inflatable envelope and both are surgically implanted beneath the skin. Periodic hypodermic injections of fluid into the puncture housing causes the envelope to progressively expand over a period of several weeks. This causes a skin flap over the envelope to "grow" and create additional skin area for a breast pouch, etc. after a mastectomy. After sufficient skin growth, the device described in that application can be removed and a normal mammary prosthesis inserted.

Because fluid is injected under high pressure into the puncture housing, it is important to (1) properly seal the puncture housing after withdrawing the needle, and (2) provide a convenient target for hypodermic puncture through the skin and housing.

In my prior U.S. Pat. No. 3,310,051, I describe a silicone capsule for implantation beneath the skin into which fluid can be injected or withdrawn by a hypodermic syringe. The puncturable capsule described in that patent works well when connected to a ventricular catheter for removing or injecting fluid into a patient's brain. However, the high pressure needed to maintain a pressure to "grow" a skin flap as described in application Ser. No. 723,338, causes such housing to leak at the needle puncture sites.

It has been proposed to utilize a plug shaped capsule that contains a silicone gel to help reseal needle puncture of a surgically implanted puncture bulb. Such device is described in U.S. Pat. No. 3,831,583. The shape and dimension of this plug-like sealant chamber is not conveniently usable with the injection angle commonly used by nurses and physicians. To gain control over subcutaneous injections, the hypodermic needle is frequently placed at a widely angled position, almost parallel to the skin. This gives the operator better control of the injection point and puncture depth than a position more perpendicular to the skin. The preferred injection position for the Skin Flap Development Device of Ser. No. 723,338 is shown in a sketch in the Heyer-Schulte Introductory Data Sheet for the Skin Flap Development Device (copy enclosed). My prior U.S. Pat. No. 3,310,351 also shows the widely angled injection position.

SUMMARY OF THE INVENTION

The present invention overcomes the problems described above and provides a subcutaneous injection housing that has a sealant chamber which can reseal needle punctures in the housing into which high pressure fluid is injected and maintained. The sealant chamber is thin, having a thickness of less than 20% of its length or width to provide a very wide angle needle injection. To aid in convenient puncturing from such wide angle, the sealant chamber is generally dome shaped.

THE DRAWINGS

DETAILED DESCRIPTION

Figure 1:
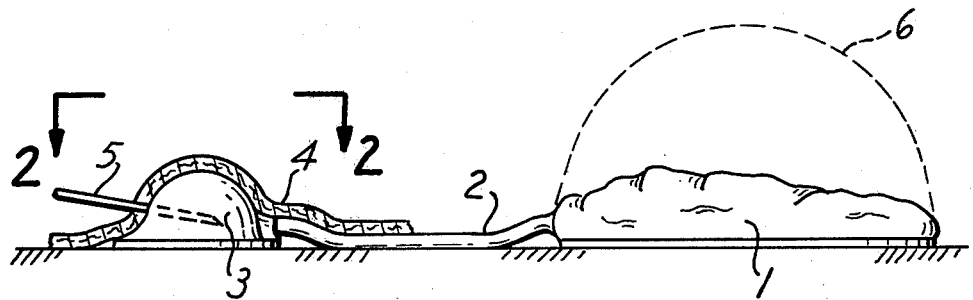
FIG. 1 is a side elevational view of a skin flap development device using the puncture housing of this invention.
Figure 2:
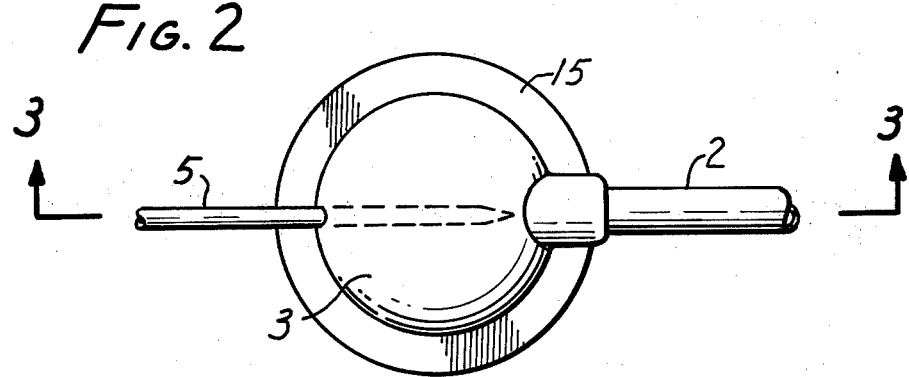
FIG. 2 is an enlarged top view of the puncture housing taken along line 2—2 of FIG. 1.

In FIG. 1, the Skin Flap Development Device is shown with a highly expandable envelope 1 connected by a tube 2 to a puncture housing 3 that is substantially nonexpandable. This device is implanted beneath skin 4 which is shown schematically as covering only the puncture housing 3. It is understood that skin 4 would also cover inflatable envelope 1. By periodic high pressure injections of fluid through needle 5, envelope 1 progressively forces the skin covering highly expandable envelope 1 to grow to the size indicated by dotted line 6.

Figure 3:
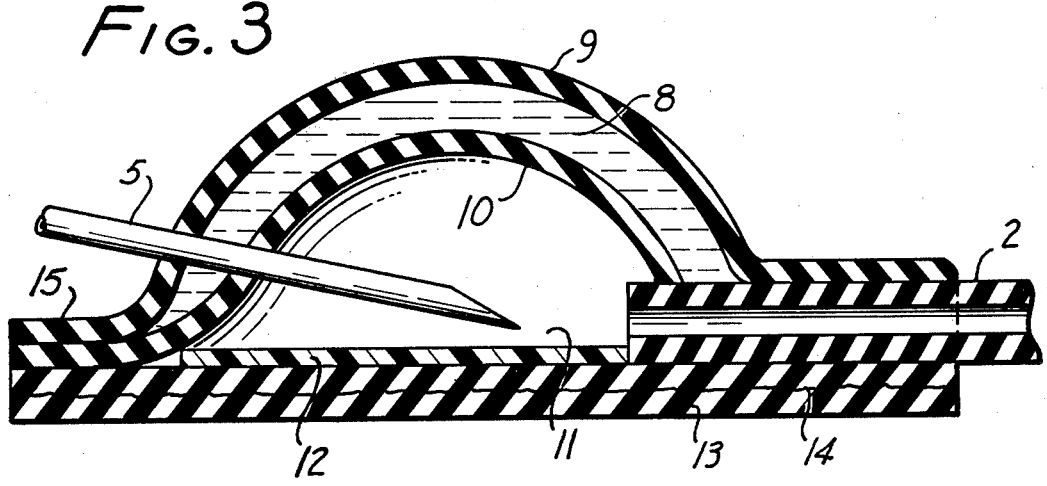
FIG. 3 is a further enlarged sectional view of the puncture housing taken along line 3—3 of FIG. 2.

The puncture housing structure is best shown in FIG. 3 in which a layer of sealant material, such as a silicone gel 8, is sandwiched between an outer wall portion 9 and an inner wall portion 10 of the puncture housing. Wall portions 9 and 10 can be of a silicone rubber material. Each wall preferably has a generally constant wall thickness. It can be seen from FIG. 3 that the sealant layer is relatively thin, and preferably has a thickness less than 20% of its length or width to provide widely angled puncture positions for the hypodermic needle.

The sealant layer 8 is in a generally dome shape so that the hypodermic needle can enter at an edge of the dome and still pass through the sealant layer 8 into a reservoir chamber 11.

If desired, a nonpuncturable plate member 12 can be provided in chamber 11 to protect puncture of the housing's base 13. For dimensional stability, a structural support member, such as a woven fabric 14, can be imbedded in the base. The dome shaped wall portions 9 and 10 are sealed to base 13 at a peripheral flange area 15.

Throughout the specification and claims, the sealant has been described as a "layer." This term is to be used in its broadest connotation and includes a highly viscous silicone gel 8 that can move around when squeezed within the sealant chamber defined by wall portions 9 and 10.

In the above description, a specific example has been used to describe this invention. However, it is understood by those skilled in the art that certain modifications can be made to this example without departing from the spirit and scope of the invention.

I claim:

1. A housing for surgical implantation having an encased sealant for repairing hypodermic punctures, wherein the improvement comprises: a generally dome shaped sealant layer sandwiched between inner and outer wall portions of the housing; and the wall portions are domed in a common direction to provide a reservoir chamber under the domed inner wall, whereby hypodermic punctures into the housing can be made through the sealant layer from widely angled positions.

2. A housing as set forth in claim 1, wherein the inner wall portion is generally dome shaped and of a generally constant wall thickness.

3. A housing as set forth in claim 1, wherein the outer wall portion is generally dome shaped and of a generally constant wall thickness.

4. A housing as set forth in claim 1, wherein the inner and outer walls are both generally dome shaped and are joined to a generally flat base.

5. A housing as set forth in claim 4, wherein the base includes a structural support member.

6. A housing as set forth in claim 5, wherein the structural support member is a fabric.

7. A housing as set forth in claim 1, wherein the inner and outer wall portions are of a silicone rubber, and the sealant is of a silicone gel.

8. A housing as set forth in claim 1, wherein the housing is substantially nonexpandable and is in flow communication with a highly expandable envelope to form a skin flap development device.

9. A housing as set forth in claim 1, wherein the housing includes a puncture stop plate to prevent puncture of an area of the housing.

10. A housing for surgical implantation having an encased sealant for repairing hypodermic punctures, wherein the improvement comprises: an outer wall portion of the housing; an inner wall portion of the housing closely spaced to the outer wall portion; and between the wall portions is a sealant layer having a generally uniform thickness in a puncture area that is substantially wider and longer than the sealant's thickness, and the puncture area of this sealant has a thickness less than 20% of its length or width, whereby hypodermic punctures into the housing can be made through the sealant layer at various locations within the puncture area from widely angled positions.

11. A housing as set forth in claim 10, wherein the sealant layer is a silicone gel.

* * * * *